United States Patent
Conte et al.

(10) Patent No.: US 6,294,200 B1
(45) Date of Patent: *Sep. 25, 2001

(54) PHARMACEUTICAL TABLET SUITABLE TO DELIVER THE ACTIVE SUBSTANCE IN SUBSEQUENT AND PREDETERMINABLE TIMES

(75) Inventors: Ubaldo Conte, Busto Arsizio; Lauretta Maggi, Pavia, both of (IT)

(73) Assignee: Jagotec AG, Hergiswil (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/795,382

(22) Filed: Feb. 4, 1997

(30) Foreign Application Priority Data

Feb. 6, 1996 (IT) ................................................ MI96A0210

(51) Int. Cl.⁷ ................................ A61K 9/24; A61K 9/20; A61K 9/28; A61K 9/30
(52) U.S. Cl. ........................... 424/472; 424/464; 424/474; 424/475
(58) Field of Search ..................................... 424/464, 472, 424/474, 475

(56) References Cited

U.S. PATENT DOCUMENTS

| 4,160,020 | | 7/1979 | Ayer et al. .............................. 424/15 |
| 4,865,849 | * | 9/1989 | Conte et al. .......................... 424/466 |
| 4,898,733 | | 2/1990 | DePrince et al. ..................... 424/425 |
| 5,213,808 | | 5/1993 | Bar-Shalom et al. ............... 424/473 |
| 5,487,901 | * | 1/1996 | Conte et al. .......................... 424/472 |
| 5,631,022 | * | 5/1997 | Mandel et al. ....................... 424/456 |

FOREIGN PATENT DOCUMENTS

| 1022171 | 3/1966 | (GB) . |
| 1346609 | 2/1974 | (GB) . |

* cited by examiner

Primary Examiner—Shelley A. Dodson
(74) Attorney, Agent, or Firm—Leydig, Voit & Mayer, Ltd

(57) ABSTRACT

Pharmaceutical tablet, capable of delivering the active substance or the active substances, according to a predeterminable release profile, comprising a core with an external partial coating in which said core consists of 3 layers, wherein the upper layer contains an amount of the active substance with suitable excipients, the intermediate layer consists of polymeric material with retarding barrier function and the lower layer contains the remaining amount of the active substance with suitable excipients and said external coating consists of controlled permeability polymeric materials, applied by compression to the lower surface and to the lateral surface of the core.

7 Claims, 1 Drawing Sheet

PHARMACEUTICAL TABLET SUITABLE TO DELIVER THE ACTIVE SUBSTANCE IN SUBSEQUENT AND PREDETERMINABLE TIMES

PRIOR ART

In the field of pharmaceutical technology, manifold are the kinds of tablets manufactured in the last years in order to obtain the release of the active substance vehiculated into them at a constant rate in time. These tablets may determine a prolonged "therapeutic covering" that is the maintenance of therapeutically effective plasmatic levels of the active substance.

Examples of such embodiments are the so called "reservoir" systems, the "OROS" osmotic pumps and the "push-pull" systems, such as those for example described in the U.S. Pat. No. 4,160,020 (1979). These systems, correctly working, imply the advantages of a possible reduction of the daily total dosage with respect to the traditional pharmaceutical forms and of a posological simplification and therefore a better acceptability for the patient.

Together with these advantages, there are both structural and functional drawbacks, which may drastically limit and/or prevent from using for long periods said systems.

The most serious disadvantages reside in that their preparation encompasses the use of rather complex polymeric materials; for example the OROS osmotic pump coating consists of insoluble polymeric material which is moreover not biodegradable in the gastrointestinal tract and this may cause accumulation phenomena in the intestine of the exhausted coatings with possible intestinal obstruction.

Lower attention has been paid to the realization of pulsating release pharmaceutical forms, in other words systems capable of releasing one or more active substances at subsequent pulses according to a program which takes into account the circadian rhythms of particular pathological symptoms.

A pharmaceutical form belonging to this type is described in the U.S. Pat. No. 4,865,849, in which a three layers pharmaceutical tablet, is characterized in that two out of these 3 layers are coated with a polymeric material impermeable and insoluble in aqueous fluids having acid pH, but soluble in an alkaline medium.

This tablet, even though innovative, cannot be manufactured on an industrial scale by using the current productive technology.

An improvement to this therapeutic system is represented by U.S. Pat. No. 5,487,901, wherein a tablet engineered for a release in subsequent times of the active substances is produced by:

a) preparing a tablet having three overlapping layers and wherein the upper layer comprises an active substance, the intermediate layer optionally contains the same or a different active substance from that contained in the upper layer, but has essentially the function of a barrier layer, finally the lower layer contains an active substance. In this three layers tablet the intermediate layer (barrier) is able to determine the time interval between the release of the first and the second dose of the drug contained in the upper and lower layers respectively.

b) completely coating the tablet by means of a film consisting of an impermeable polymeric material.

c) removing the polymeric coating from the upper surface (recognizable since it shows a prominent portion) of the tablet by abrasion thus allowing the immediate release of the active substance quantity contained in said upper layer.

Also this realization shows nevertheless productive drawbacks determined by the fact that, during the abrasion phase, a part of the active substance contained in the upper layer is removed with possible negative repercussions on the uniformity of the content of the tablets. A further complication may reside in the polymeric material used for the coating, which, although being biocompatible and biodegradable, may request, for the biodegradability, a prolonged period of time and cause the possible persistence of the empty coating in the final tract of the intestine.

SUMMARY

The pharmaceutical tablet capable of releasing the active substance in subsequent and predeterminable times according to the present invention allows to overcome the drawbacks of the prior art. Said tablet is characterized by the following structure:

a) a core consisting of three layers and obtained by compression, in which
   the upper layer contains an active substance which is immediately released when the tablet comes into contact with an aqueous medium or with gastric or intestinal fluid;
   the intermediate layer optionally containing the active substance has a suitable composition to form a barrier able to determine a time interval between the release of the active substance contained in the upper layer and the one contained in the lower layer;
   the lower layer may present the same or a different formulation from that of the upper layer, the same or a different active substance from that contained in the upper layer, and it may be formulated to have the release of the active substance with a prefixed kinetics;

b) a polymeric coating of the lower and lateral surface of said core, optionally coating an active substance, obtained by compression, able to form a barrier impermeable to the aqueous medium for a predeterminable period of time.

The tablet so obtained may be optionally further coated by a polymeric film soluble in water or in aqueous fluids.

This tablet is prepared by the following procedure:
in the first step the three layers core is produced by a compression procedure;
in the second step the core is coated by compression on the lower and lateral surface with suitable polymeric materials having controlled permeability formulated with excipients able to give the mass suitable compressibility characteristics.

According to a further embodiment of the present invention the core consists of two layers, wherein the upper layer is the barrier-layer and the lower layer contains the fast release active substance, said tablet being covered by said impermeable coating on the lateral and lower surface while on the upper surface a layer containing the fast release active substance is applied.

According to another further embodiment of the present invention the three layers core is characterized by being covered on the lateral and the lower surface by said impermeable coating, whereas on the upper surface of the upper layer comprising the fast release active substance a further layer containing the fast release active substance is applied.

BRIEF DESCRIPTION OF THE FIGURES

The tablet according to the present invention is illustrated by the following figures.

DETAILED DESCRIPTION OF THE INVENTION

Figure 1:
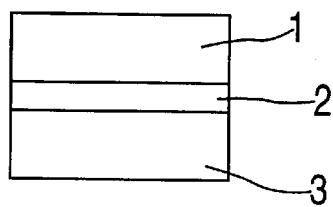
FIG. 1 shows the core of the tablet in which (1) represents the upper layer, (2) represents the intermediate layer and (3) represents the lower layer.

The pharmaceutical tablet object of the present invention allows the release of active substances in subsequent and predeterminable times and it is characterized by the following structure:

a) a core (FIG. 1) consisting of 3 layers in which:
  the upper layer (1) contains an active substance vehiculated with excipients able to assure a fast release of the active substance when the tablet comes into contact with an aqueous medium or with gastric or intestinal fluid;
  the intermediate layer (2), or barrier-layer, shows a composition based on biocompatible and biodegradable polymeric materials able to form a barrier which determines a time interval between the release of the active substance contained in the upper layer (1) and the one contained in the lower layer (3); said intermediate layer preferably does not contain the active substance; in any case said intermediate layer acts as a "timer" for the release of the substance contained in the lower layer. Said barrier layer has fundamentally the task of slowly (in a time interval programmable "in vitro") interacting with the dissolution medium, thus protecting the third layer from the contact with the dissolution medium for a predeterminable period of time;
  the lower layer (3) may have the same or a different composition from that of the upper layer, contain the same or a different active substance from the one contained in the upper layer, in any case this layer is able to allow the release of the active substance according to a program predeterminable by suitable in vitro tests;

b) a coating (4) (FIG. 2) applied on the lower and lateral surface of said core by a compression procedure, consisting of a polymeric material able to form a layer impermeable to the aqueous medium for a period of time predeterminable by suitable in vitro tests.

Said coating shows a strength to the erosion and/or to the gelification and/or to the dissolution able to assure an adequate protection of the core from the contact with the external medium for the period of time necessary to the release of the active substance both from the upper layer and from the lower layer.

Figure 3:
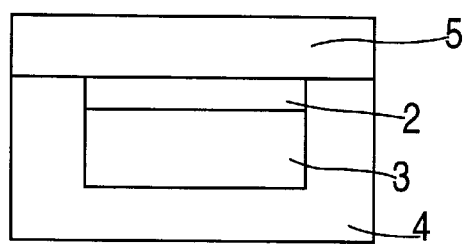
FIG. 3 shows a tablet with a two layer core having the coating (4) on the lower and lateral surface and the coating (5) on the upper surface.
Figure 4:
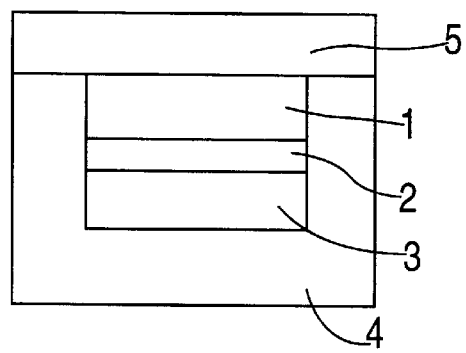
FIG. 4 shows a tablet having the coating (4) on the lower and lateral surface and the coating (5) on the upper surface.

The tablet according to the present invention may be produced in other forms without going outside the scope and the limits of the invention, for example as disclosed in FIGS. 3 and 4 wherein the layers (1), (2), (3) and the coating (4) have the already described meaning and the coating (5) contains an active substance and is characterized by having a composition able to allow the fast release of the active substance itself.

The tablets described in the present invention may be easily produced using highly automated compression procedures, as far as the preparation both of the core and of the coating are concerned.

Figure 2:
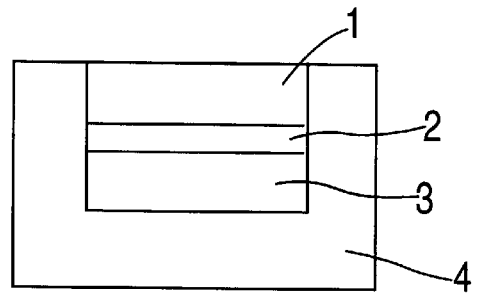
FIG. 2 shows a tablet having the coating (4) on the lower and lateral surface.

In particular the partially coated three layers core tablets represented in FIG. 2 are produced by a compression procedure in two distinct steps. In the first step the three layers core is obtained by means of a compressing machine of Manesty-Layer-press type.

In the second step said three layers core undergoes a partial coating by using a suitably equipped (Kilian-Centra-Cota kind or Korsch-Central Core Coater 3C) compressing machines. Both these machines are able to take said cores and place them correctly and centrally into the matrix where the granulate or the powder is deposited for the partial coating of said core; subsequently the machine automatically provides for the final compression for the coating of the core for the obtainment of the tablet as represented in FIG. 2.

By this process a tablet is prepared with a portion of the surface of layer 1 (corresponding to the upper surface of said layer) immediately available for the contact with aqueous liquids and then able to quickly release the active substance while the remaining portion of the tablet (corresponding to lateral surface of the layers 1 and 2 and the lateral and lower surface of layer 3) results homogeneously and regularly coated by a layer of polymeric material impermeable to the aqueous medium for a specified period of time. As already noticed the tablet may show other configurations which are pointed out for example in the FIGS. 3 and 4.

In fact the central core may also consist of a two layer tablet, that is the layer 2 with barrier functions and the layer 3 containing the active substance as illustrated in the FIG. 3. This core is coated by compression, on the upper part by a fast disintegration and dissolution coating 5 containing an active substance quantity which is quickly released and on the lateral surface of layer 2 whereas on the lateral and lower surface of layer 3 by the coating 4 which forms a barrier impermeable for a specified period of time.

In any case the tablet core according to the present invention has a suitable geometrical shape to be subjected to the coating process by compression.

The preferred realization of the tablet according to the present invention is represented in FIG. 2, wherein the layer (1), quickly disintegrable and/or soluble, when comes into contact with the aqueous liquids (both "in vitro" and "in vivo") allows first the release of the active substance, after the activation of the process of hydration and progressive gelification/erosion of the barrier layer 2 and, finally, after a time interval depending on the composition and the thickness of said barrier layer 2, the controlled release of the active substance contained in the layer 3.

For the formulation of said layer 1, beside the active substance, suitable compounds are used to increase the disintegration of said layer facilitating in this way the dissolution (fast release) of the vehiculated active substance.

Said compounds are preferably selected from the group consisting of cross-linked polyvinylpyrrolidone, hydroxypropylcellulose and hydroxypropylmethylcellulose having low and medium molecular weight, cross-linked sodium carboxymethylcellulose, carboxymethylstarch, potassium methacrylate-divinylbenzene copolymer, polyvinylalcohols, starches, starches derivatives, microcryistalline cellulose and cellulosic derivatives, beta cyclodextrine and generally dextrines derivatives, mannitol, lactose, sorbitol and xylitol and mixtures thereof. Said substances form from 1.0 to 90% the weight of the layer and, preferably, from 20 to 70%.

Moreover adjuvant substances consisting of the so called effervescent mixtures may be used, namely substances able to produce the fast disintegration of the layer when it comes into contact with aqueous liquids and, preferably, with gastric juice.

Among these substances we mention sodium and other alkali or alkaline-earth metals carbonates and bicarbonates, glycocoll sodium carbonate and other pharmaceutically acceptable salts capable of producing effervescence in an acid environment.

Depending on the pH of the medium during the disintegration of the layer, other substances such as citric, tartaric and fumaric acid may be added to the tablet according to the present invention, in order to determine the appearance of the "effervescence" and the fast disintegration.

Also adjuvant substances normally employed in the pharmaceutical technique may be used such as diluents, buffers, binders, adsorbents, lubricants etc. and particularly starch, pregelified starch, calcium phosphate, mannitol, lactose, sucrose, glucose, sorbitol, microcristalline cellulose and binding agents such as gelatin, polyvinylpyrrolidone, methylcellulose, starch, ethylcellulose, arabic gum, tragacanth gum, magnesium stearate, stearic acid, colloidal silica, glyceryl monostearate, polyoxyethylenglycols having molecular weight from 400 to 50000, hydrogenated castor oil, waxes and mono-di and tri-substituted glycerides.

The formulation of the layer 2 or barrier layer, which forms the element allowing to determine the time interval before the release of the active substance contained in the layer 3, comprises polymers, adjuvant and plasticizing substances.

The polymers of the barrier layer are preferably selected from the group consisting of hydroxypropylmethylcellulose with molecular weight ranging from 1,000 and 4,000,000, hydroxypropylcellulose with molecular weight from 2,000 to 2,000,000, carboxyvinylpolymers, polyvinyl alcohols, glucans, scleroglucans, mannans, galactomannans, carrageenin and carrageenans, xanthans, alginic acid and derivatives thereof, pectine, amylose, poly(methyl vinyl ethers/maleic anhydride), carboxymethylcellulose and derivatives thereof, ethylcellulose, methylcellulose and in general cellulosic derivatives and mixtures thereof.

Said polymeric substances are present in a percentage ranging from 5 to 90% of the total weight of said layer and preferably range from 50 to 90%.

The adjuvant substances are preferably selected from the group consisting of glyceryl monostearate and derivatives thereof, semi-synthetic triglycerides, semi-synthetic glycerides, hydrogenated castor oil, glycerylpalmitostearate, glyceryl behenate, cetilic alcohol, polyvinylpyrrolidone, glycerin, ethylcellulose, methylcellulose, sodium carboxymethylcellulose, mixtures thereof and other natural or synthetic substances well known to anyone skilled in the field. For example magnesium stearate, stearic acid, talc, sodium benzoate, boric acid, polyoxyethylenglycols and colloidal silica are employed.

Moreover diluent, binding substances, lubricants, buffering agents, anti-adherents, gliding substances and other substances capable of giving said layer the desired characteristics maybe used, like those used later-on in the examples.

The plasticizing substances are preferably selected from the group consisting of hydrogenated castor oil, fatty acids, substituted glycerides and triglycerides, polyoxyethylenglycols and derivatives thereof having different molecular weight, ranging from 400 to 60,000. They have the function to give the barrier layer the necessary elasticity and improve its compressibility, adhesion and cohesion characteristics.

The adjuvant substances, in association with the previously reported polymeric materials, are able to better define the protection time exerted by the barrier, this interval ranging from 15 minutes to more than 6–8 hours according to the therapeutic needs requested.

This layer 3 may have the same composition as the layer 1 and contain the same or a different active substance from that contained in layer 1 or may contain a mixture of more active substances which are released after a determined time interval from the release of the active substance contained in layer 1.

Depending on the therapeutic requirements of the active substance contained in said layer 3, the layer can contain substances able to modify (to slow) the release of said active substances in a predeterminable time interval by suitable in vitro tests.

According to the preferred embodiment illustrated in FIG. 2, the three layer core is partially coated, by compression, with a uniform coating 4 comprising polymeric material impermeable to water and/or to aqueous fluids for the period of time needed for the release of the active substance both from the layer 1 and from the layer 3. Said period of time is predeterminable by in vitro tests.

Said coating comprises also adjuvant substances, plasticizing substances, lubricants, antiadherents etc. namely substances capable of giving good mechanical and workability characteristics.

The polymeric material for said coating is preferably selected from the group consisting of: hydroxypropylmethylcellulose having molecular weight ranging from 1,000 to 4,000,000, hydroxypropylcellulose having molecular weight ranging from 2,000 to 2,000,000, carboxyvinyl polymers, polyvinylalcohols, glucans, scleroglucans, mannans, galactomannans, carrageenin and carrageenans, xanthans, alginic acid and salts thereof with alkali and alkaline-earth metals, pectine, amylose and derivatives thereof, poly (methyl vinyl ethers/maleic anhydride), carboxymethylcellulose and derivatives thereof, ethylcellulose, methylcellulose, acrylic and methacrylic copolymer (with different solubility characteristics dependent or independent from the pH of the medium), cellulose acetophthalate, cellulose acetopropionate, cellulose trimellitate and other natural synthetic and/or semisynthetic derivatives of cellulose, methylcellulose, hydroxypropylcellulose, hydroxypropylmethylcellulose and derivatives thereof, and mixture thereof.

Said polymeric substances are present in a percentage of from 5 to 90% of the total weight of said coating and preferably from 40 to 90%.

In the formulation of the coating adjuvant substances are used preferably selected from the group consisting of glyceryl monostearate and semi-synthetic triglycerides derivatives, semi-synthetic glycerides, hydrogenated castor oil, glycerylpalmitostearate, glyceryl behenate, cetilic alcohol, polyvinylpyrrolidone, glycerin, ethylcellulose, methylcellulose, sodium carboxymethylcellulose and other natural or synthetic substances well known to anyone skilled in the field. For example magnesium stearate, stearic acid, talc, sodium benzoate, boric acid, polyoxyethylenglycols and colloidal silica, are used.

Moreover plasticizing substances are used preferably selected from the group consisting of hydrogenated castor oil, fatty acids, substituted glycerides and triglycerides, polyoxyethylenglycols and derivatives thereof having different molecular weight, normally ranging from 400 to 60,000 and mixture thereof.

They have the function to impart the material forming the coating the necessary elasticity and improve the compressibility thereof, adhesion and cohesion characteristics.

Moreover diluents, binding agents, lubricants, buffering, antiadherents, gliding substances and other substances able to give said layer the requested characteristics may be used like those disclosed later-on in the examples.

Acting as reported above, tablets may be obtained coated by compression in any part of the surface except for the upper face, as reported in FIG. 2. This means that the whole surface of the core results out to be impermeable to aqueous liquids except the upper face.

The tablets so obtained may undergo a further filming process, according to the traditional procedures, using a polymeric coating easily soluble and/or dispersible in water and/or in aqueous fluids depending on the pH of the medium, which does not modify the release characteristics of the finished system. Said polymeric coating may be formed by natural polymers such as shellac, sandarac gum or synthetic ones such as hydroxypropylmethyl cellulose, hydroxypropylcellulose, methylcellulose, polyvinylpyrrolidone, the acrylic and methacrylic copolymer (with different solubility characteristics dependent or independent from the pH of the medium), cellulose acetophthalate, cellulose acetopropionate, cellulose trimellitate and other derivatives well known to those skilled in the field.

If the coating film is gastroresistant and enterosoluble, the release of the active substance vehiculated into said first layer, can only occur at the duodenal level and the release of the active substance contained in the third layer may occur at the level of the distal part of the intestinal tract (at the colon level). Said coating involves the whole surface of the tablet and it is applied by using the basin or the fluidized bed technique.

As better pointed out in the examples, the tablet according to the invention coming into contact with water and/or gastric fluid and/or intestinal fluid is able to release immediately a first part of the active substance while the second part of the active substance is released in subsequent times depending on the characteristics of the barrier layer.

The preferred size of the various components of the tablet are the following:
  core diameter: 4–12 mm, preferably 6–9 mm
  thickness of the layers 1 and 3: 2–8 mm, preferably 3–4 mm
  thickness of the layer 2: 0.4–4.0 mm, preferably 0.8–2.0 mm.

The outer coating shows a thickness of from 0.5 to 4.0 mm but preferably from 1.0 to 2.0 mm and it corresponds to 5–70% by weight of the total tablet weight.

These measures are absolutely indicative and not binding, since the tablets according to the present invention may have different geometrical shapes such as oval, ovoidal, ellipsoidal or asymmetrical shape.

The active substance which may be employed in the tablets according to the present invention is any substance having biopharmaceutical and/or pharmacodynamical variations dependent on the circadian cycle and the substances able to fulfill their therapeutic and/or protective action against pathological manifestations which show variations according to temporal and in particular circadian rhythms; for example steroidal, non-steroidal anti-inflammatories (NSAIDs) such as sodium diclofenac, indomethacin, ibuprofen, ketoprofen, diflunisal, piroxicam, naproxen, flurbiprofen, sodium tolmetin, substances having antibiotic activity such as ampicillin, amoxycillin, cephradine, clavulanic acid, cefaclor, cefalexin, cloxacillin, erythromycin, their salts and derivatives thereof, substances having antimicrobic activity at the urogenital level such as nitrofurantoin, nalidixic acid, oxolinic acid, pipemidic acid, and derivatives thereof; sleep inducing substances and tranquilizers such as diazepam, nitrazepam, flurazepam, oxazepam, chlordiazepoxide, medazepam, lorazepam, active substances for the prevention of anginous attacks and hypertensive attacks such as diltiazem, trapidil, urapidil, benziodarone, dipyridamole, lidoflazine, naphthydrofurile oxalate, perhexilline maleate, oxyphedrine hydrochloride and antihistaminic and/or antiasthmatic drugs such as ephedrine, terfenadine, theophylline, chlorpheniramine, terbutaline, metaproterenol, aminophylline, isoprenaline, salbutamol, methylprednisolone, dexamethasone ibopamine and combinations thereof; antiviral drugs such as acyclovir, gangliocyclovir, ribavirine, zoliuvidine or AZT; H2 antagonists anti-ulcer drugs: cimetidine, famotidine, nizatidine, ranitidine, roxatidine, sucralfate; drugs active at cardiovascular level such as: acebutol, metoprolol, atenolol, nadolol, oxprenolol, bevantolol, bopindol, pindolol, labetolol, propranolol, mepindolol, sotalol; calcium antagonists such as: amlodipine, nitrendipine, nifedipine, nicardipine, verapamil; ACE-inhibitors: captopril, enalapril, or substances having diuretic activity such as hydrochlorothiazide, chlorthalidone, indapamide, piretamide, xipamide; or organic nitrates: glyceryl trinitrate, isosorbide dinitrate, isosorbide 5-mononitrate and antiparkinson drugs such as Levodopa, carbidopa, benserazide.

The tablets according to the invention may be produced from granular mixtures having a granulometry lower than 710 $\mu$m using the productive technologies currently in use and then by a production process immediately transferable on industrial scale.

The three layer core, is produced using rotating compressing machines able to produce "multilayer" tablets such as for example Manesty Layer-press (Liverpool, UK).

Normally the working pressure ranges from 800 to 5000 kg. The three layers core is then coated applying the coating material by compression, by using a rotating compressing machine, with a pressure of from 800 to 5000 kg, as it will be better understood in the examples. Optionally the tablet so obtained is completely coated with a soluble film dependent on the pH of the medium.

EXAMPLE 1

Preparation of a series of (5,000) tablets as represented in FIG. 2, containing Ranitidine hydrochloride as active substance.

1-a—Preparation of the Granulate Containing the Active Substance

A granulate is prepared which is used in the preparation of the layers (1) and (3). Each layer, which contains 150 mg of active substance, has the following unit composition:

| | |
|---|---|
| Ranitidine HCl (U.S.P. grade) equal to 150 mg of ranitidine | 167.4 mg |
| Cornstarch (USP grade, C. Erba, Milan, I) | 40.0 mg |
| Polyvinylpyrrolidone (Plasdone$^R$ K30, ISP, Wayne, NY, USA) | 4.0 mg |
| Carboxymethyl starch (Explotab$^R$, E. Mendell Co. Inc., Carmel, NY, USA) | 35.0 mg |
| Magnesium stearate (USP grade, C. Erba, Milan, I) | 5.0 mg |
| Total | 239.4 mg |

In a sigma mixer mod. Erweka K 5 type (Frankfurt a. M.—D), suitable amounts of the active substance and cornstarch are mixed; the mixture is wet by using a 10% (w/v) alcoholic solution of polyvinylpyrrolidone and the homogeneously wet mass is forced onto a 25 mesh (710 $\mu$m) grid thereby obtaining a regular granulate which is dried in a 40–45° C. air circulation stove. The granulate, dried up to a constant weight, is placed in a Turbula T2A mod. (Bachofen—Basel—CH) powder mixer and added with carboxymethylstarch and mixed for 20 minutes. Magnesium stearate is then added to the mixture and the mixing is carried on for further 20 minutes. The granulate undergoes the compression stage as described below.

1-b—Preparation of the Granulate for the Barrier Layer (2)

An amount of granulate necessary for the achievement of No. 5000 barrier layers having the following per cent composition is prepared:

| | |
|---|---:|
| Hydroxypropylmethylcellulose (Methocel$^R$ E5 Premium, Colorcon, Orpington, UK) | 76.5 |
| Hydrogenated castor oil (Cutina HR, Henkel, Düsseldorf, D) | 19.0 |
| Polyvinylpyrrolidone (Plasdone$^R$ K29-32 ISP, Wayne, NY, USA) | 2.9 |
| Green lacquer (Eigenmann Veronelli, Milan, I) | 0.1 |
| Magnesium stearate (USP grade, C. Erba, Milan, I) | 1.0 |
| Colloidal silica (Syloid 244, Grace GmbH, Worms, D) | 0.5 |
| Total | 100.0 |

In a sigma Erweka K5 type mod. (Frankfurt am M., D) mixer the proper amounts of hydroxypropylmethyl cellulose (Methocel E 5: apparent viscosity 5 cps), hydrogenated castor oil and green lacquer are mixed; the mixture is wet with a 10% w/v hydro-alcoholic solution of polyvinylpyrrolidone and the homogeneously wet mass is forced onto a 25 mesh (710 μm) grid, thereby obtaining a regular granulate, of light green colour, which is dried in a 40–45° C. air circulation stove. The granulate, dried up to a constant weight, is placed in a (Turbula T2A mod.) powder mixer and added with magnesium stearate and colloidal silica and mixed for 20 minutes. The granulate undergoes the compression stage as described below.

1-c—Preparation of the Three Layer Cores (by compression)

The granulates obtained according to what reported above are loaded in the three charging hoppers of a rotating compressing machine suitable to produce three layers tablets (e.g. Manesty Layer-Press, Liverpool, UK). In particular in the first and third hopper the granulate described at point 1-a is loaded while the second hopper is filled up with the granulate described at point 1-b.

The compressing machine is equipped with circular convex punches having a diameter equal to 9 mm and R=12 mm. The machine is adjusted in order to produce three layer cores formed by a first 239.4 mg amount of granulate containing the active substance (equal to 150 mg of ranitidine) a 100 mg barrier layer (such an amount being necessary to obtain a thickness of about 1.0 mm) and a second 239.4 mg quantity of granulate containing the active substance (corresponding to 150 mg of ranitidine).

Operating at 3,000 kg pressure three layer cores having an average weight equal to 578.8 mg containing two distinct quantities of active substance (150 mg each), in the layer 1 and in the layer 3 are respectively obtained. The cores so obtained undergo a second compression stage for the application of the partial coating using the granulate described at point 1-d.

1-d—Preparation of the Granulate for the External Coating

An amount of granulate necessary for the achievement of No. 5000 coatings having, each, the following percentage composition is prepared:

| | |
|---|---:|
| Hydroxypropylmethylcellulose (Methocel$^R$ K4M, Colorcon, Orpington, UK) | 46.0 |
| Mannitol | 46.0 |
| Polyvinylpyrrolidone (Plasdone$^R$ K29-32 Gaf Corp., Wayne, NY, USA) | 6.3 |
| Red + blue lacquer (Eigenmann-Veronelli, Milan, I) | 0.2 |
| Magnesium stearate (USP grade, C. Erba, Milan, I) | 1.0 |
| Colloidal silica (Syloid 244, Grace GmbH, Worms, D) | 0.5 |
| Total | 100.0 |

In a sigma Erweka K5 type mod. (Frankfurt am M., D) mixer the proper amounts of hydroxypropylmethyl cellulose (Methocel K4M: apparent viscosity 4000 cps), mannitol and red-blue lacquer are mixed; the mixture is wet with a 10% w/v hydro-alcoholic solution of polyvinylpyrrolidone and the homogeneously wet mass is forced onto a 25 mesh (710 μm) grid obtaining a regular granulate, of violet color, which is dried in a 40–45° C. air circulation stove. The granulate, dried to a constant weight, is placed in a (Turbula T2A mod.) powder mixer and added with magnesium stearate and colloidal silica and mixed for 20 minutes. The granulate, undergoes the compression stage as described below.

1-e—Partial Coating by Compression of the Cores

The granulate obtained according to point 1-d is loaded in the first charging hopper of a rotating compressing machine suitable to produce the so called dry-coated tablets (e.g. Kilian Centra-Cota or Korsch-Central Core Coater 3C type). In order to obtain the tablets illustrated in FIG. 2, the second hopper does not contain granulate. the compressing machine is equipped with circular convex punches having a diameter equal to 12 mm and R=12 mm. The machine is adjusted to produce in-lay tablets with quantities of 220 mg of granulate for the coating layer. The machine is likewise equipped with a transfer system allowing the transfer of the three layer cores prepared as pointed out at point 1-c and the exact positioning in the matrix, in which the amount of granulate necessary for the coating has already been supplied. Automatically the machine provides for the perfect centering of said core and for the progressive compression which enables the progressive sinking of the core in the powder bed constituted by the granulate 1-d and finally the achievement of the coated tablet.

Operating at about 3000 kg pressure the tablets are obtained illustrated in FIG. 2 consisting of a three layers core (two out of these layers contain 150 mg of ranitidine each) coated on the surface except for the upper face of the layer 1.

1-f—Dissolution Test

In order to estimate the release characteristics of the tablets, the equipment 2, paddle (described in USP XXII) is used operating at 100 r.p.m. and using deionized water at 37° C. as the dissolution fluid. The release of the active substance is followed by U.V. spectrophotometric determination at 313 nm using an automatic sampling and reading system (Spectracomp 602, Advanced Products—Milan, I).

The results are reported in Table I.

TABLE 1

| TIME (min) | % released active substance |
|---:|---:|
| 10 | 41.0 |
| 20 | 47.5 |
| 30 | 50.0 |

TABLE 1-continued

| TIME (min) | % released active substance |
|---|---|
| 60 | 51.3 |
| 90 | 54.9 |
| 120 | 72.6 |
| 150 | 88.5 |
| 180 | 95.1 |
| 210 | 98.1 |
| 240 | 99.8 |

It is possible to point out that from the tablets a fast release of the first amount of active substance (47.5% of the total dose contained into the tablets) in 20 minutes is obtained, an interval of about 80 minutes during which a negligible amount of active substance is released and the subsequent fast release of the second quantity of active substance after 90 minutes from the beginning of the dissolution test. Such a behaviour fully answers the aims of the present invention.

EXAMPLE 2

Preparation of a series of tablets (5,000) as represented in FIG. 3, containing Ranitidine hydrochloride as the active principle.

A thickness of the barrier layer 2 able to determine a more prolonged time interval between the release of the first and the second quantity of active substance, with respect to what has been reported in the Example 1 has been realized.

2-a—Preparation of the Granulate Containing the Active Substance (Ranitidine hydrochloride)

The preparation is carried out as described in example 1 at point 1-a.

2-b—Preparation of the Granulate for the Barrier Layer 2

The preparation is carried out as reported in example 1 at point 1-b.

2-c—Preparation of Two Layer Cores (by compression)

The granulates obtained according to what reported at points 2-a and 2-b are loaded into the two hoppers of a rotating compressing machine suitable to produce two layer tablets (e.g. Manesty Layer-Press, Liverpool, UK). In particular in the first hopper the granulate described at point 2-a is loaded while the second hopper is filled up with the granulate described at point 2-b.

The compressing machine is equipped with circular convex punches having a diameter equal to 9 mm and R=12 mm. The machine is adjusted to produce two layer cores, wherein the layer 3 formed by 239.4 mg of granulate containing the active substance (equal to 150 mg of ranitidine) and the barrier layer 2 consisting of 130 mg of the relative granulate (such an amount being necessary to obtain a thickness of about 1.2 mm). Two layer cores having an average weight equal to 369.4 mg containing 150 mg of active substance are obtained. The cores so obtained undergo a second compression stage for the application of the coating again using the granulate described at point 2-a for the coating 5 and the granulate described at the point 2-d for the coating 4.

2-d—Preparation of the Granulate for the Coating

The preparation is carried out as reported in example 1 at point 1-d.

2-e—Coating by Compression of the Cores

The granulate obtained according to what described at point 2-d is loaded into the first hopper of a rotating compressing machine suitable to produce the so called dry-coated tablets (e.g. Kilian Centra-Cota or Korsch-Central Core Coater 3C type), whereas, in the second hopper the granulate is loaded containing the active principle Ranitidine hydrochloride, described at point 2-a.

The compressing machine is equipped with circular convex punches having a diameter equal to 12 mm and R=12 mm. The machine is adjusted to produce dry-coated tablets as illustrated in FIG. 3, in which the coating 4 consists of granulate described at the point 2-d and the coating 5 consists of the granulate described at point 2-a. The hopper feeding the transfer system of the cores is loaded with the two layer cores prepared as indicated at point 2-c. The machine provides for the transfer and the exact positioning of the cores in the matrix into which the amount of granulate necessary for the coating 4 has already been supplied. Automatically the machine provides for the perfect centering of the cores, for a precompression stage which enables the sinking of the core in the granulate bed constituting the coating and for the loading of the granulate for the coating 5 and then it provides for the final compression of the system which allows the achievement of a tablet as reported in FIG. 3. Operating as described in example 1 the tablets consisting of a two layers core, coated by two different kinds of granulate are thus obtained. The first, of impermeable kind, covers the tablet except for the upper surface, while the second one containing the active substance covers the upper face.

2-f—Dissolution Test

The dissolution test is carried out as described in example 1 at point 1-f.

The results are reported in Table II.

TABLE II

| TIME (min) | % released |
|---|---|
| 10 | 44.4 |
| 20 | 48.2 |
| 30 | 49.1 |
| 60 | 50.1 |
| 90 | 51.4 |
| 120 | 52.8 |
| 150 | 54.1 |
| 180 | 80.9 |
| 210 | 93.8 |
| 240 | 98.8 |

It is possible to point out that from the tablets of example 2 a fast release of the first amount of active substance (49.1% of the total dose contained into the system) in 30 minutes is obtained, an interval of more than 2 hours during which a negligible amount of active substance is released and the subsequent fast release of the second amount of active substance after 2 hours and 30 minutes from the beginning of the dissolution test. Such a behaviour fully answers the aims of the present invention.

EXAMPLE 3

Preparation of a series of tablets (5,000) as represented in FIG. 2, containing sodium diclofenac as active substance.

3-a—Preparation of the Granulate Containing the Active Substance

A granulate is prepared, according to the patterns farther on described, which is used in the preparation of the layers 1 and 3. Each layer, which contains 75 mg of active substance, has the following unit composition:

| | |
|---|---:|
| Sodium diclofenac (Secifarma, Milan, I) | 75.0 mg |
| Cornstarch (C. Erba, Milan, I) | 90.0 mg |
| Sodium lauryl sulfate (USP grade, C. Erba, Milan, I) | 0.2 mg |
| Methylcellulose (Methocel A 4 C, Colorcorn Orpington, UK) | 0.4 mg |
| Carboxymethyl starch (Explotab$^R$, E. Mendell Co., Carmel, NY, USA) | 6.0 mg |
| Crosslinked polyvinylpyrrolidone (Polyplasdone XL, ISP, Wayne, NY, USA) | 3.8 mg |
| Magnesium stearate (C. Erba, Milan, I) | 1.0 mg |
| Total | 176.4 mg |

In a sigma mixer mod. Erweka K 5 type (Frankfurt a. M.—D), suitable amounts of the active substance and cornstarch are mixed; the mixture is wet by a 1.3% w/v aqueous solution of methylcellulose into which the sodium lauryl sulfate had been previously dissolved; the homogeneously wet mass is forced onto a 25 mesh (710 μm) grid obtaining a regular granulate which is dried in a 40–45° C. air circulation stove. The granulate, dried to a constant weight, is placed in a Turbula T2A mod. (Bachofen—Basel—CH) powder mixer and added with carboxymethylstarch and crosslinked polyvinylpyrrolidone and mixed for 20'. Magnesium stearate is then added to the mixture and mixing is carried out for further 20 minutes. The granulate, analyzed as far as the active principle content is concerned, undergoes the compression stage as described below.

3-b—Preparation of the Granulate for the Barrier Layer 2

An amount of granulate necessary for the achievement of No. 5000 barrier layers having the following percentage composition is prepared:

| | |
|---|---:|
| Hydroxypropylmethylcellulose (Methocel$^R$ E3 Premium, Colorcon, Orpington, UK) | 76.5 |
| Hydrogenated castor oil (Cutina HR, Henkel, Düsseldorf, D) | 19.0 |
| Polyvinylpyrrolidone (Plasdone$^R$ K29-32 ISP, Wayne, NY, USA) | 2.9 |
| Green lacquer + blue lacquer (Eigenmann Veronelli, Milan, I) | 0.1 |
| Magnesium stearate (USP grade, C. Erba, Milan, I) | 1.0 |
| Colloidal silica (Syloid 244, Grace GmbH, Worms, D) | 0.5 |
| Total | 100.0 |

In a sigma Erweka K5 type mod. (Frankfurt am M., D) mixer the proper amounts of hydroxypropylmethyl cellulose (Methocel E 3: apparent Viscosity 3 cps), hydrogenated castor oil, blue lacquer and green lacquer are mixed; the mixture is wet with a 10% w/v hydro-alcoholic solution of polyvinylpyrrolidone and the homogeneously wet mass is forced onto a 25 mesh (710 μm) grid obtaining a regular granulate, of dark green colour, which is dried in a 40–45° C. air circulation stove. The granulate, dried up to a constant weight, is placed in a (Turbula T2A mod.) powder mixer and added with magnesium stearate and colloidal silica and mixed for 20'. The granulate, undergoes compression as described below.

3-c—Preparation of the Three Layer Cores (by compression)

The preparation is carried out as reported in example 1 at point 1-c. The compressing machine, equipped with circular convex punches having a diameter equal to 9 mm and R=12 mm is adjusted to produce three layers cores formed by a layer 1 having 176.4 mg of granulate 3-a containing the active substance (equal to 75 mg of diclofenac), a layer 2 having 100 mg of granulate 3-b (such an amount being necessary to obtain a thickness of about 1.0 mm) and a layer 3 having 176.4 mg of granulate 3-a containing the active substance (equal to 75 mg of diclofenac). Operating as described, three layers cores having an average weight equal to 452.8 mg containing two distinct amounts of active principle (each corresponding to 75 mg), in layer 1 and in layer 3 are respectively obtained. The cores so obtained undergo a second compression stage for the application of the partial coating using the granulate described at point 3-d.

3-d—Preparation of the Granulate for the External Coating

The preparation is carried out as reported in example 1 at point 1-d.

3-e—Partial Coating by Compression of the Cores

The coating of the cores is carried out as reported in example 1 at point 1-e.

Tablets, as illustrated in FIG. 2, are obtained consisting of a three layers core (two out of these 3 layers contain 75 mg each of diclofenac), coated on the surface except for the upper face of the first layer characterized by a quick release of the active principle.

3-f—Dissolution Test

In order to estimate the release characteristics of the tablets, the experiment 2, paddle (described in USP XXII) is used operating at 100 r.p.m. and using deionized water at 37° C. as the dissolution fluid. The release of the active substance is followed by U.V. spectrophotometric determination at 276 nm using an automatic sampling and reading system (Spectracomp 602, Advanced Products—Milan, I).

The results are reported in Table III.

TABLE III

| TIME (min) | % release |
|---:|---:|
| 15 | 27.9 |
| 30 | 39.9 |
| 45 | 49.3 |
| 60 | 49.9 |
| 90 | 50.2 |
| 120 | 52.0 |
| 150 | 61.7 |
| 180 | 78.0 |
| 210 | 95.4 |
| 240 | 100.5 |

It is possible to point out that from the tablets a fast release of the first amount of active substance (49.3% of the total dose) in 45 minutes is obtained, an interval of about 90 minutes during which a negligible amount of active substance is released and the subsequent fast release of the second amount of active substance after 2.5 hours from the beginning of the dissolution test. Such a behaviour fully answers the aims of the present invention.

EXAMPLE 4

Preparation of a series (5,000) of tablets as reported in example 3, containing sodium diclofenac as active principle, using a different composition for the external coating.

4-a—Preparation of the Granulate containing the Active Substance

The preparation is carried out as reported in example 3 at point 3-a.

4-b—Preparation of the Granulate for the Barrier Layer 2

The preparation is carried out as reported in example 3 at point 3-b.

4-c—Preparation of the Three Layer Cores (by compression)

The preparation is carried out as reported in example 3 at point 3-c.

4-d—Preparation of the granulate for the External Coating

An amount of granulate is prepared necessary for the achievement of No. 5,000 coatings having, each, the following percentage composition:

| | |
|---|---|
| Hydroxypropylmethylcellulose (Methocel$^R$ K100M, Colorcon, Orpington, UK) | 79.0 |
| Hydrogenated castor oil (Cutina HR, Henkel, Düsseldorf, D) | 13.3 |
| Polyvinylpyrrolidone (Plasdone$^R$ K29-32 Gaf Corp., Wayne, NY, USA) | 6.0 |
| Orange lacquer (Eigenmann-Veronelli, Milan, I) | 0.2 |
| Magnesium stearate (USP grade, C. Erba, Milan, I) | 1.0 |
| Colloidal silica (Syloid 244, Grace GmbH, Worms, D) | 0.5 |
| Total | 100.0 |

In a sigma Erweka K5 type mod. (Frankfurt am M., D) mixer the proper amounts of hydroxypropylmethyl cellulose (Methocel K100M: apparent viscosity 100000 cps), mannitol and orange lacquer are mixed; the mixture is wet with a 10% w/v hydro-alcoholic solution of polyvinylpyrrolidone and the homogeneously wet mass is forced onto a 25 mesh (710 μm) grid, thereby obtaining a regular granulate, of orange colour, which is dried in a 40–45° C. air circulation stove. The granulate, dried to a constant weight, is placed in a Turbula T2A mod. powder mixer and added with magnesium stearate and colloidal silica and mixed for 20 minutes. The granulate, undergoes compression as described below.

4-e—Coating by Compression of the Cores

The coating is carried out as reported in example 1 at point 1-e, using the granulate described at point 4-d.

Tablets, as illustrated in FIG. 2, are obtained consisting of a three layers (two out of these 3 layers contain 75 mg each of diclofenac), coated on the surface except for the upper face corresponding to the first layer showing fast release of the active substance.

4-f—Dissolution Test

The test is carried out as described in the Example 3 at the point 3-f. The results are reported in Table IV.

TABLE IV

| TIME (min) | % released |
|---|---|
| 15 | 24.6 |
| 30 | 38.9 |
| 45 | 47.6 |
| 60 | 50.3 |
| 90 | 51.2 |
| 120 | 51.7 |
| 150 | 52.9 |
| 180 | 60.1 |
| 210 | 75.8 |
| 240 | 89.9 |
| 270 | 97.5 |
| 300 | 100.7 |

It is possible to point out that from the tablets a fast release of the first amount of active substance (47.6% of the total dose contained into the tablet) in 45 minutes is obtained, an interval of about 2 hours during which a negligible amount of active substance is released and the subsequent fast release of the second amount of active substance after 2 hours and 30 minutes from the beginning of the dissolution test. Such a behaviour fully answers the aims of the present invention.

EXAMPLE 5

Preparation of a series of (5,000) tablets as represented in FIG. 2, containing ibuprofen as active substance.

5-a—Preparation of the Granulate Containing the Active Substance

A granulate is prepared, according to the patterns farther on described, which is used in the preparation of the layers 1 and 3. Each layer, which contains 150 mg of active substance, has the following unit composition:

| | |
|---|---|
| Ibuprofen (Francis, Milan, I) | 150.0 mg |
| Cornstarch (C. Erba, Milan, I) | 44.8 mg |
| Methylcellulose (Methocel A 4 C, Colorcon Orpington, UK) | 0.8 mg |
| Crosslinked polyvinylpyrrolidone (Polyplasdone$^R$ XL, Gaf Corp., Wayne, NY, USA) | 4.5 mg |
| Carboxymethylstarch (Explotab$^R$, Mendell, Carmel, NY, USA) | 11.2 mg |
| Magnesium stearate (C. Erba, Milan, I) | 1.9 mg |
| Total | 213.2 mg |

In a sigma mixer mod. Erweka K 5 type (Frankfurt a. M.—D), suitable amounts of the active substance and cornstarch are mixed; the mixture is wet by a 1% (w/v) aqueous solution of methylcellulose and the homogeneously wet mass is forced onto a 25 mesh (710 μm) grid obtaining a regular granulate which is dried in a 40–45° C. air circulation stove. The granulate, dried to a constant weight, is placed in a Turbula T2A mod. (Bachofen—Basel—CH) powder mixer, added with crosslinked polyvinylpyrrolidone, carboxymethylstarch and mixed for further 20'. Magnesium stearate is then added to the mixture and the mixing is carried out for further 20 minutes. The granulate undergoes compression as described below.

5-b—Preparation of the Granulate for the Barrier Layer 2

The preparation is carried out as reported in example 1 at point 1-b.

5-c—Preparation of the Three Layer Cores (by compression)

The granulate obtained according what previously reported are loaded into the three hoppers of a rotating compressing machine suitable to produce three layer tablets (e.g. Manesty Layer-Press, Liverpool, UK). In particular in the first and in the third hopper the granulate described at point 5-a is loaded; while the second hopper is filled with the granulate described at point 5-b.

The compressing machine is equipped with circular convex punches having a diameter equal to 9 mm and R=12 mm. The machine is adjusted to produce three layers cores and precisely: layer 1 formed by 213.2 mg of granulate containing the active substance (equal to 150 mg of ibuprofen), layer 2 constituted by 100 mg of the granulate for the barrier layer (such an amount being necessary to obtain a thickness of about 1.0 mm) and layer (3) constituted by 213.2 mg of granulate containing the active substance (equal to 150 mg of ibuprofen). Three layers cores are obtained having an average weight equal to 526.4 mg containing two distinct amounts of active substance (each amount of active substance corresponding to 150 mg). The cores so obtained undergo a second compression stage for the application of the partial coating using the granulate described at point 5-d.

5-d—Preparation of the Granulate for the External Coating

The preparation is carried out as reported in example 4 at point 4-d.

5-e—Coating by Compression of the Cores

The coating is carried out as reported in example 1 at point 1-e, using the barrier granulate as described at point 5-d.

The tablets, as illustrated in FIG. 2, are obtained consisting of a three layers core (two out of said three layers contain 150 mg each of ibuprofen), coated on the surface except for the upper face corresponding to the first layer showing the fast release of the active substance.

5-f—Dissolution Test

In order to estimate the release characteristics of the tablets the eqipment 2, paddle (described in USP XXII) is used operating at 100 r.p.m. and using simulated intestinal fluid (according to USP XXIII), pH=7.5 at 37° C. as the dissolution fluid. The release of the active substance is followed by U.V. spectrophotometric determination at 223 nm using an automatic sampling and reading system (Spectracomp 602, Advanced Products—Milan, I).

The results reported in Table V.

TABLE V

| TIME (min) | % released |
|---|---|
| 15 | 47.8 |
| 30 | 50.0 |
| 60 | 51.2 |
| 90 | 51.9 |
| 120 | 52.4 |
| 150 | 52.8 |
| 180 | 53.1 |
| 210 | 53.5 |
| 240 | 63.3 |
| 270 | 101.4 |
| 300 | 101.6 |

It is possible to point out that from the tablets a fast release of the first quantity of active substance (50% of the total dose) in 30 minutes is obtained, an interval of about 3 hours during which a negligible amount of active substance is released and the subsequent fast release of the second quantity of active substance after 3 hours and 30 minutes from the beginning of the dissolution test. Such a behaviour fully answers the aims of the present invention.

EXAMPLE 6

Preparation of a series of (5,000) tablets as illustrated in FIG. 2, containing ibuprofen as active substance.

6-a—Preparation of the Granulate Containing the Active Substance for the Layers 1 and 3

The preparation is carried out as reported in example 5 at point 5-a.

6-b—Preparation of the Granulate for the Barrier Layer 2

An amount of granulate necessary for the achievement of No. 5000 barrier layers having the following percentage composition is prepared:

| | |
|---|---|
| Hydroxyrpropylmethylcellulose (Methocel$^R$ E50 Premium, Colorcon, Orpington, UK) | 76.5 |
| Hydrogenated castor oil (Cutina HR, Henkel, Düsseldorf, D) | 19.0 |
| Polyvinylpyrrolidone (Plasdone$^R$ K29-32 ISP, Wayne, NY, USA) | 2.9 |
| Yellow lacquer (Eigenmann Veronelli, Milan, I) | 0.1 |
| Magnesium stearate (USP grade, C. Erba, Milan, I) | 1.0 |
| Colloidal silica (Syloid 244, Grace GmbH, Worms, D) | 0.5 |
| Total | 100.0 |

In a sigma Erweka K5 type mod. (Frankfurt am M., D) mixer the proper amounts of hydroxypropylmethyl cellulose (Methocel E 50: apparent Viscosity 50 cps), hydrogenated castor oil and yellow lacquer are mixed; the mixture is wet with a 10% w/v hydro-alcoholic solution of polyvinylpyrrolidone and the homogeneously wet mass is forced onto a 25 mesh (710 μm) grid obtaining a regular granulate, of yellow colour, which is dried in a 40–45° C. air circulation stove. The granulate, dried to a constant weight, is placed in a Turbula T2A mod. powder mixer and added with magnesium stearate and colloidal silica and the mixing is carried on for 20'. The granulate, undergoes compression as described below.

6-c—Preparation of the Three Layer Cores (by compression)

The preparation is carried out as reported in example 5 at point 5-c, using for the barrier layer 2 the granulate described at point 6-b. Three layers cores having an average weight equal to 527.4 mg containing two distinct amounts of active substance, each weighing 150 mg. The cores so obtained undergo a second compression for the application of the external coating using the granulate described at the point 6-d.

6-d—Preparation of the Granulate for the External Coating

An amount of granulate necessary for the achievement of No. 5,000 coatings having the following percentage composition is prepared:

| | |
|---|---|
| Hydroxypropylmethylcellulose (Methocel$^R$ K15M, Colorcon, Orpington, UK) | 79.0 |
| Hydrogenated castor oil (Cutina HR, Henkel, Düsseldorf, D) | 13.3 |
| Polyvinylpyrrolidone (Plasdone$^R$ K29-32, ISP, Wayne, NY, USA) | 6.0 |
| Red lacquer (Eigenmann-Veronelli, Milan, I) | 0.2 |
| Magnesium stearate (USP grade, C. Erba, Milan, I) | 1.0 |
| Colloidal silica (Syloid 224, Grace GmbH, Worms, D) | 0.5 |
| Total | 100.0 |

In a sigma Erweka K5 type mod. (Frankfurt am M., D) mixer the proper amounts of hydroxypropylmethyl cellulose (Methocel K15M: apparent viscosity 15000 cps), mannitol and red lacquer are mixed; the mixture is wet with a 10% w/v hydro-alcoholic solution of polyvinylpyrrolidone and the homogeneously wet mass is forced onto a 25 mesh (710 μm) grid obtaining a regular granulate, of pink colour, which is dried in a 40–45° C. air circulation stove. The granulate, dried to a constant weight, is placed in a (Turbula T2A mod.) powder mixer and added with magnesium stearate and colloidal silica and the mixing is carried on for 20'. The granulate undergoes compression as described below.

6-e—Coating by Compression of the Cores

The coating of the cores is carried out as reported in example 1 at point 1-e, using the granulate described at point 6-d.

Tablets, as illustrated in FIG. 2, are obtained consisting of a three layers core (two out of three layers contain 150 mg each of ibuprofen) coated on the surface except for the upper face corresponding to the first layer showing the fast release of the active substance.

6-f—Dissolution Test

The test is carried out as reported in example 5 at point 1-f. The results are reported in Table VI.

TABLE VI

| TIME (min) | % release |
|---|---|
| 15 | 45.4 |
| 30 | 47.8 |
| 60 | 49.6 |
| 120 | 50.0 |
| 180 | 50.2 |
| 240 | 50.6 |
| 300 | 50.8 |
| 360 | 50.9 |
| 420 | 51.2 |

TABLE VI-continued

| TIME (min) | % release |
|---|---|
| 480 | 51.3 |
| 540 | 77.2 |
| 600 | 89.3 |
| 660 | 98.7 |
| 720 | 100.2 |

It is possible to point out that from the tablets a fast release of the first amount of the active substance (45.4% of the total dose) in 15 minutes is obtained, an interval of about 7 hours and 30 minutes during which a negligible amount of active substance is released and the subsequent fast release of the second quantity of active substance after 8 hour from the beginning of the dissolution test. Such a behaviour fully answers the aims of the present invention.

EXAMPLE 7

Preparation of a series of (5,000) tablets as in FIG. 2, containing a mixture of Levodopa and Carbidopa as active substance.

7-a—Preparation of the Granulate for the Layer 1

A first granulate is prepared which will be used in the preparation of the layer 1. The layer 1 contains 30 mg of Carbidopa and 30 mg of Levodopa and shows the following unit composition:

| | |
|---|---|
| Carbidopa monohydrate = 30 mg of Carbidopa (Alfa Chem, Milan, I) | 32.4 mg |
| Levodopa (Alfa Chem, Milan, I) | 30.0 mg |
| Microcrystalline cellulose (Avicel PH 102, FMC, Philadelphia, USA) | 99.2 mg |
| Green lacquer + yellow lacquer (Eigenmann-Veronelli, Milan, I) | 0.2 mg |
| Polyvinylpyrrolidone (Plasdone$^R$ K 30, ISP, Wayne, NY, USA) | 4.8 mg |
| Carboxymethylstarch (Explolab$^R$, Mendell, Carmel, NY, USA) | 12.0 mg |
| Talc (C. Erba, Milan, I) | 6.9 mg |
| Magnesium stearate (C. Erba, Milan, I) | 2.4 mg |
| Colloidal silica (Syloid 244, Grace GmbH, Worms, D) | 1.2 mg |
| Total | 188.2 mg |

In a sigma Erweka K5 type mod. (Frankfurt am M., D) mixer, the proper amounts of the two active substances with the microcristalline cellulose and the two dyes are mixed; the mixture is wet with a 10% (w/v) hydro-alcoholic solution of polyvinylpyrrolidone and the homogeneously wet mass is forced onto a 25 mesh (710 μm) grid obtaining a regular granulate which is dried in a 40–45° C. air circulation stove. The granulate, dried to a constant weight, is placed in a Turbula T2A mod. (Bachofen—Basel—CH) powder mixer, added with carboxymethylstarch and mixed for 20 minutes. Talc, magnesium stearate and colloidal silica are then added to the mixture and the mixing is carried out for further 20 minutes. The granulate undergoes the compression as described below.

7-b—Preparation of the Granulate for the Layer 3

A second granulate which will be used in the preparation of the layer 3 is prepared. The layer 3 contains 25 mg of Carbidopa and 100 mg of Levodopa and shows the following unit composition:

| | |
|---|---|
| Carbidopa monohydrate = 25 mg of Carbidopa (Alfa Chem, Milan, I) | 27.0 mg |
| Levodopa (Alfa Chem, Milan, I) | 100.0 mg |
| Microcristalline cellulose (Avicel PH 102, FMC, Philadelphia, USA) | 50.0 mg |
| Green lacquer (Eigenmann-Veronelli, Milan, I) | 0.1 mg |
| Polyvinylpyrrolidone (Plasdone$^R$ K30, ISP, Wayne, NY, USA) | 6.0 mg |
| Carboxymethylstarch (Explotab$^R$, Mendell, Carmel, NY, USA) | 14.0 mg |
| Talc (C. Erba, Milan, I) | 6.0 mg |
| Magnesium stearate (C. Erba, Milan, I) | 4.0 mg |
| Colloidal silica (Syloid 244, Grace GmbH, Worms, D) | 1.0 mg |
| Total | 208.0 mg |

In a sigma Erweka K5 type mod. (Frankfurt am M., D) mixer the proper amounts of the two active principles with the microcristalline cellulose and the dye are mixed; the mixture is wet with a 10% (w/v) hydro-alcoholic solution of polyvinylpyrrolidone and the homogeneously wet mass is forced onto a 25 mesh (710 μm) grid obtaining a regular granulate which is dried in a 40–45° C. air circulation stove. The granulate, dried to a constant weight, is placed in a Turbula T2A mod. (Bachofen—Basel—CH) powder mixer, added with carboxymethylstarch and mixed for 20 minutes. Talc, magnesium stearate and colloidal silica are then added to the mixture and the mixing is carried out for further 20 minutes. The granulate, undergoes compression as described below.

7-c—Preparation of the Granulate for the Barrier Layer 2

The preparation is carried out as reported in example 3 at point 3-b.

7-d—Preparation of the Three Layer Cores (by compression)

The granulate obtained according to what previously reported is loaded into the three hoppers of a rotating compressing machine suitable to produce three layer tablets (e.g. Manesty Layer-Press, Liverpool, UK). In particular in the first hopper the granulate described at point 7-a is loaded, in the second hopper the granulate described at point 7-c is loaded and the third hopper is filled with the granulate described at point 7-b.

The compressing machine is equipped with circular convex punches having a diameter equal to 9 mm and R=12 mm. The machine is adjusted to produce three layers cores of which the layer 1 is formed by 188.2 mg of granulate 7-a containing 30 mg of Carbidopa and 30 mg of Levodopa, the layer 2 consists of 130 mg of the granulate 7-c (such an amount being necessary to obtain a thickness of about 1.2 mm) and the layer 3 is constituted by 208.0 mg of granulate 7-b containing 25 mg of Carbidopa and 100 mg of Levodopa.

Operating as previously described, three layers cores are obtained having an average weight equal to 526.2 mg containing two distinct amounts of the association of the two active substances for a total of 55 mg of Carbidopa and 130 mg of Levodopa. The cores so obtained undergo a second compression stage for the application of the coating using the granulate described at point 7-e.

7-e—Preparation of the Granulate for the External Coating

The preparation is carried out as reported in example 1 at point 1-d.

7-f—Coating by Compression

The coating is carried out as reported in example 1 at point 1-e. Tablets, as illustrated in FIG. 2, are obtained consisting of three layers cores (two out of three layers contain two different amounts of the association of the two active substances: Carbidopa and Levodopa), coated on the surface except the upper face constituted by the first layer showing fast release of the first fraction of active substances.

7-g—Dissolution Test

In order to estimate the release characteristics of the tablets the equipment 2, paddle (described in USP XXII) is used operating at 100 r.p.m. and using deionized water at 37° C. as the dissolution fluid. The release of the two active substances is followed by U.V. spectrophotometric determination at 280 nm using an automatic sampling and reading system (Spectracomp 602, Advanced Products—Milan, I).

The results are reported in Table VII.

TABLE VII

| TIME (min) | % Carbidopa released | % Levodopa released |
| --- | --- | --- |
| 15 | 53.9 | 21.0 |
| 30 | 55.4 | 23.0 |
| 60 | 55.6 | 23.2 |
| 90 | 55.9 | 23.4 |
| 120 | 56.0 | 23.6 |
| 150 | 58.0 | 27.2 |
| 180 | 98.2 | 97.6 |
| 210 | 99.3 | 99.2 |
| 240 | 100.2 | 99.9 |

It is possible to point out that from the tablets a fast release of the first amount of Carbidopa (equal to 53.9% of the total dose) in 15 minutes is obtained, an interval of about 60–90 minutes during which a negligible amount of active substance is released and the subsequent fast release of the second amount of Carbidopa after 2 hours from the beginning of the dissolution test. At the same time a fast release of the first amount of Levodopa (equal to 21% of the total dose) in 15 minutes is obtained, an interval of about 2 hours and 20 minutes during which a negligible amount of active substance is released and the subsequent fast release of the second quota of Levodopa after 3 hours from the beginning of the dissolution test.

Such a behavior fully answers the aims of the present invention.

What is claimed is:

1. A tablet for pharmaceutical use suitable to release the active substances in subsequent and predetermined times, comprising a three layered core covered by a partial coating layer, said core having the following structure:

an upper layer consisting of active substance and suitable excipients to allow a fast release of the active substance when the tablet comes into contact with an aqueous medium;

an intermediate layer whose composition comprises polymeric material suitable to form a barrier able to determine a time interval between the release of the active substance contained in the upper layer and the active substance contained in the lower layer, a lower layer comprising one or more active substances and having the same or a different composition as the upper layer, said lower layer allowing the controlled release of said active substances;

and wherein said partial coating layer consists of granulated polymeric substances, adjuvant substances and plasticizing agents applied by compression on the whole lateral surface and on the lower base of said three layered core thus forming an impermeable barrier which resists dissolution for a predetermined period of time while allowing for the release of the active substance both from the upper layer and from the lower layer, said polymeric substances being selected from hydroxypropylmethylcellulose having viscosity between 4,000 and 100,000 cP when measured at 20° C. in a 2% aqueous solution.

2. A tablet for pharmaceutical use according to claim 1 wherein the adjuvant substance used in the formulation of the partial coating layer is polyvinylpyrrolidone.

3. The tablet as claimed in claim 1, wherein said polymeric substances of said partial coating are present in a percentage of from 5 to 90% with respect to the total weight of said coating.

4. The tablet as claimed in claim 1, wherein said partial coating forms from 5 to 70% of the total weight of the tablet and shows a thickness of from 0.5 to 4.0 mm.

5. The tablet as claimed in claim 1, wherein said polymeric substance of said partial coating is hydroxypropylmethylcellulose having a viscosity of 4,000 cP.

6. The tablet as claimed in claim 1, wherein said polymeric substance of said partial coating is hydroxypropylmethylcellulose having a viscosity of 15,000 cP.

7. The tablet as claimed in claim 1, wherein said polymeric substance of said partial coating is hydroxypropylmethylcellulose having a viscosity of 100,000 cP.

* * * * *